(12) United States Patent (10) Patent No.: US 7,578,782 B2
Miles et al. (45) Date of Patent: Aug. 25, 2009

(54) METHODS AND SYSTEMS FOR DETERMINING A VISCOSITY OF A FLUID

(75) Inventors: Scott D. Miles, Sandy, UT (US); Gill B. Beamson, Salt Lake City, UT (US); Gordon B. Jacobs, Salt Lake City, UT (US)

(73) Assignee: World Heart, Inc., Oakland, CA (US)

( * ) Notice: Subject to any disclaimer, the term of this patent is extended or adjusted under 35 U.S.C. 154(b) by 505 days.

(21) Appl. No.: 11/138,041

(22) Filed: May 26, 2005

(65) Prior Publication Data

US 2005/0214131 A1 Sep. 29, 2005

Related U.S. Application Data

(63) Continuation-in-part of application No. 10/225,906, filed on Aug. 21, 2002, now Pat. No. 6,949,066.

(51) Int. Cl.
*A61N 1/362* (2006.01)
(52) U.S. Cl. .................. 600/16; 623/3.1; 417/420; 415/900
(58) Field of Classification Search ............. 600/16–18, 600/300, 368; 417/63, 420; 415/900; 623/3.1
See application file for complete search history.

(56) References Cited

U.S. PATENT DOCUMENTS

| | | | |
|---|---|---|---|
| 4,517,830 A | 5/1985 | Gunn et al. | |
| 4,554,821 A | 11/1985 | Kiesewetter et al. | |
| 5,576,306 A | 11/1996 | Dressman et al. | |
| 5,629,209 A | 5/1997 | Braun, Sr. et al. | |
| 5,725,357 A | 3/1998 | Nakazeki et al. | |
| 5,789,393 A | 8/1998 | Dressman et al. | |
| 5,792,660 A | 8/1998 | Spillert et al. | |
| 5,798,454 A | 8/1998 | Nakazeki et al. | |
| 5,925,043 A | 7/1999 | Kumar et al. | |
| 5,968,542 A | 10/1999 | Tipton | |
| 5,979,229 A | 11/1999 | Barnikol | |
| 6,019,735 A | 2/2000 | Kensey et al. | |
| 6,074,180 A | 6/2000 | Khanwilkar et al. | |
| 6,142,752 A * | 11/2000 | Akamatsu et al. ............ | 623/3.1 |
| 6,152,888 A | 11/2000 | Kensey et al. | |
| 6,238,719 B1 | 5/2001 | Fox | |
| 6,261,244 B1 | 7/2001 | Kensey et al. | |
| 6,270,831 B2 | 8/2001 | Kumar et al. | |
| 6,322,525 B1 | 11/2001 | Kensey et al. | |

(Continued)

*Primary Examiner*—Scott M Getzow
(74) *Attorney, Agent, or Firm*—Holland & Hart, LLP

(57) ABSTRACT

Methods for determining a viscosity of a fluid passing through a fluid pump are disclosed. An amount of energy associated with axially moving a rotor may be determined and correlated to a viscosity of fluid interacting therewith. For example, energy associated with a response of a suspended rotor may be determined. The amount of energy may be correlated with a viscosity of the fluid interacting with the rotor. The rotor may be initially unsuspended and an amount of energy associated with suspending the rotor may be determined and correlated with a viscosity of fluid interacting with the rotor. In another method, subsequent to suspending a rotor, the rotor may be unsuspended and an energy response of the rotor may be quantified to determine a viscosity of fluid passing through the pump. Systems for determining a viscosity of a fluid are also disclosed.

36 Claims, 10 Drawing Sheets

U.S. PATENT DOCUMENTS

| | | |
|---|---|---|
| 6,394,769 B1 | 5/2002 | Bearnson et al. |
| 6,443,911 B1 | 9/2002 | Kensey et al. |
| 6,450,974 B1 | 9/2002 | Kim et al. |
| 6,595,762 B2 | 7/2003 | Khanwilkar et al. |
| 6,659,965 B1 | 12/2003 | Kensey et al. |
| 6,692,437 B2 | 2/2004 | Kensey et al. |
| 6,709,390 B1 | 3/2004 | Marie Pop |
| 6,711,943 B1 | 3/2004 | Schöb |
| 6,733,769 B1 | 5/2004 | Ryan et al. |
| 6,796,168 B1 | 9/2004 | Goldstein et al. |
| 6,805,125 B1 | 10/2004 | Crump et al. |
| 6,805,674 B2 | 10/2004 | Kensey et al. |
| 6,879,126 B2 | 4/2005 | Paden et al. |

* cited by examiner

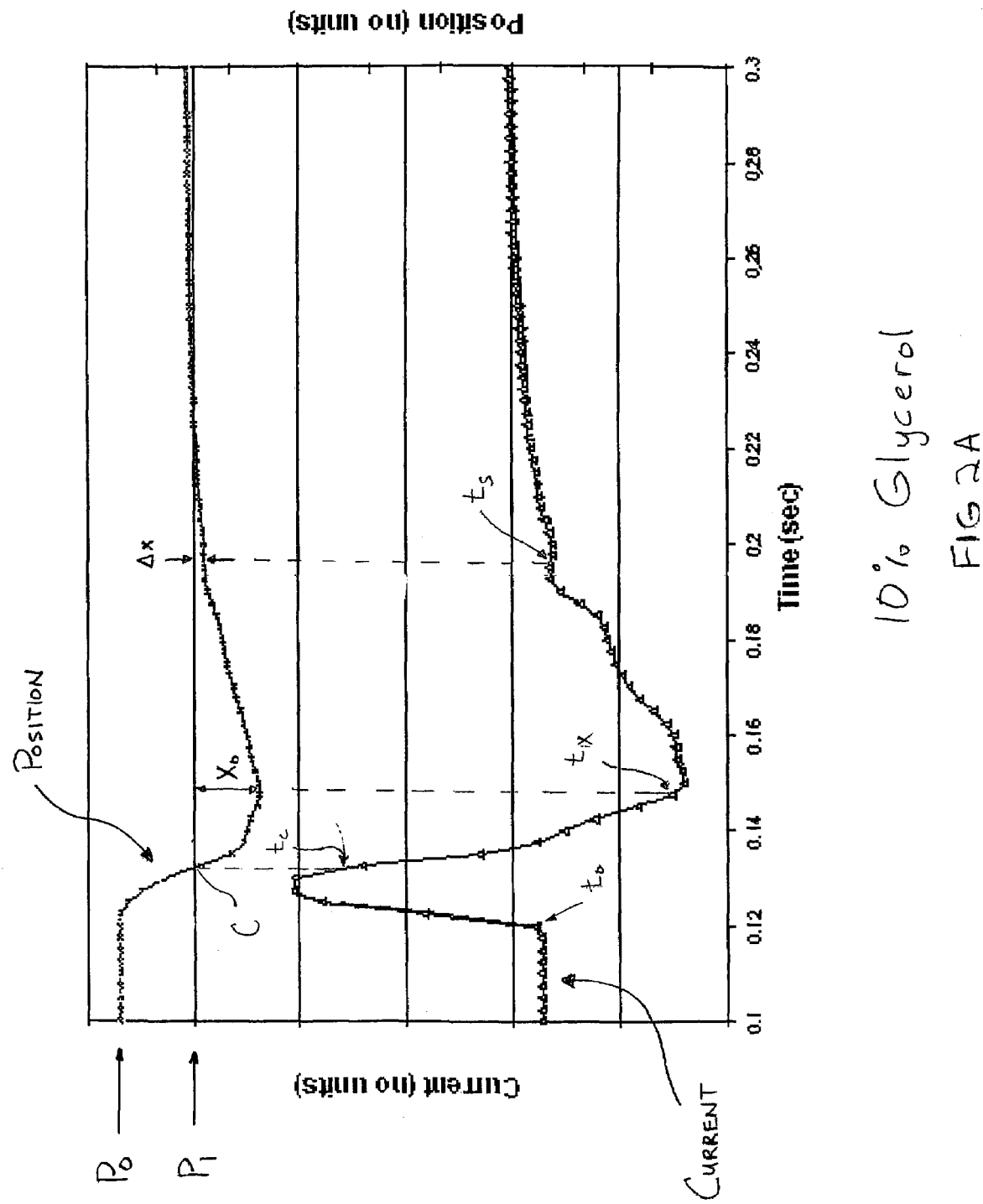
FIG 2A 10% Glycerol

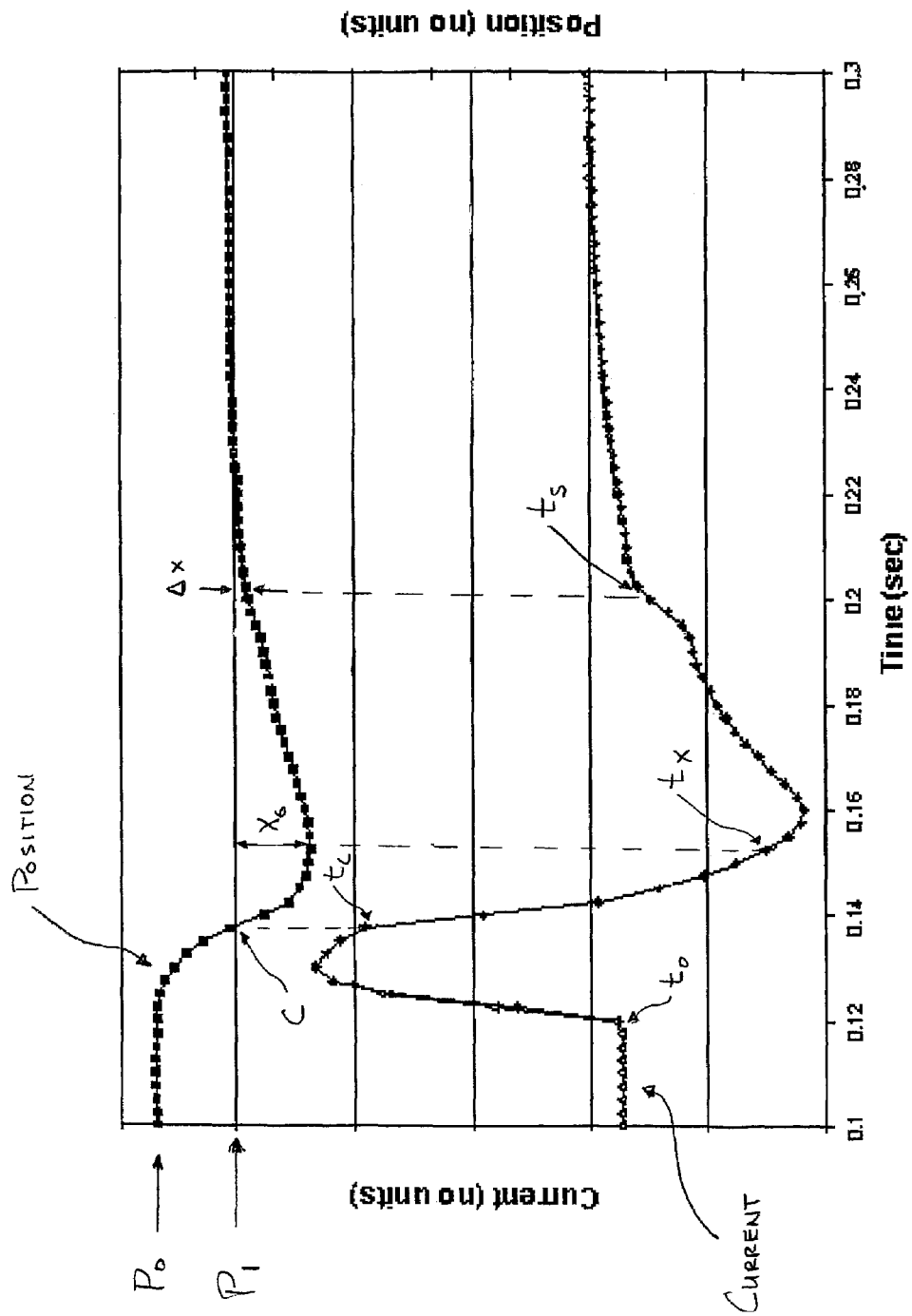

METHODS AND SYSTEMS FOR DETERMINING A VISCOSITY OF A FLUID

RELATED APPLICATIONS

This application is a continuation-in-part of U.S. patent application Ser. No. 10/225,906, filed Aug. 21, 2002 now U.S. Pat. No. 6,949,066 which is assigned to the assignee of the present invention and the disclosure of which is incorporated, in its entirety, by reference herein.

TECHNICAL FIELD OF THE INVENTION

This invention relates to systems and pump devices including a magnetically suspended rotor and methods of operation thereof. More particularly, the present invention relates to methods, systems, and devices for determining a viscosity of a fluid interacting with a magnetically suspended rotor of a pump device.

BACKGROUND OF THE INVENTION

Pumps for implantation in a human patient for long or short-term use as ventricular assist devices (VADs) or complete heart replacement have been explored for some time. It is also well known that pumps for corrosive fluids, blood, and fluids used in food processing may require careful design of the flow passages to avoid fluid damage, contamination, and other undesirable conditions. Accordingly, VADs with magnetically suspended rotors have been developed. Relative to blood pumps, for example, U.S. Pat. Nos. 6,074,180 and 6,394,769, each assigned to the assignee of the present invention and the disclosure of each of which is incorporated, in its entirety, by reference herein, disclose VADs.

With respect to the operation of blood pumps, it is desirable to know the flow rate of blood passing through the blood pump. For example, knowledge of the flow rate through a blood pump may be useful for diagnosing the status of one or more of the following: the performance of the natural heart and related cardiovascular system including things such as, pulse rate, ejection fraction, contractility, opening or closing of the aortic valve or other valves of the heart, operation of valves included in an VAD or similar pump system (e.g., LVAD, RVAD, TAH, BiVAD, etc.), blood flow provided by the natural heart, contractility of the natural heart, hemodynamic condition of the patient, blood flow through a VAD, or properties of the blood.

In order to estimate the flow of blood through a VAD or other blood pump, it is desirable to know the viscosity of the blood. This may allow for a more accurate estimation of the flow through a blood pump. In implantable blood pumps such as left ventricular assist devices (LVADs), conventional approaches have incorporated separate blood flow meters that are implanted with the LVAD. In other conventional systems, no blood flow meter is employed, but other external means are used to make determinations of blood flow, such as, for instance, pump performance, or physiologic state of the patient.

Thus, as mentioned above, one parameter that may be of interest in controlling a pump device having a magnetically suspended rotor is the viscosity of the fluid passing therethrough. Viscosity is a measure of a resistance of a fluid to deformation under shear stress. The viscosity of a liquid is generally related to interaction between constituents comprising the liquid. Generally, a viscosity of a liquid is relatively independent of pressure (except at very high pressure) and usually decreases as a temperature of the liquid increases. Viscosities of liquids are typically several orders of magnitude higher than viscosities of gases.

However, some fluids, such as blood, may include various suspensions, liquids, solids, or cells. In further detail, blood is a suspension which may include red blood cells, white blood cells, and platelets in a plasma of gases, salts, proteins, carbohydrates, and lipids. The viscosity of blood generally increases as the percentage of red blood cells in the blood increases because more red blood cells increase internal friction of the blood, which corresponds to a greater viscosity. The ratio of the volume of packed red blood cells to the volume of whole blood is referred to as the hematocrit. A typical hematocrit of about 40 (that is, approximately 40% of the blood volume is red blood cells and the remainder plasma), may generally correspond to a viscosity of whole blood which is about 2.5 to 3 times a viscosity of water. A hematocrit of about 60 or 70, which may often occur in patients with polycythemia, or abnormally high red blood cell counts, a blood viscosity may become as high as 10 times that of water. Alternatively, when the hematocrit falls drastically, as may occur in patients with anemia (i.e., indicating decreased number of red cells in the blood), blood viscosity can approach that of plasma alone. Further, although the concentrations and types of proteins in plasma can influence the viscosity thereof, such concentrations usually have relatively limited, if any, effect on the overall viscosity of whole blood. Of course, drugs may influence a viscosity of blood.

In an effort to eliminate the need for a conventional, separate flow meter, algorithms that estimate the flow of blood through the blood pump have been created, for example, such algorithms are described in U.S. patent application Ser. No. 10/225,906. These algorithms generally utilize information obtained from the electrical signals used to power the motor that rotates the pump rotor to estimate a flow rate of blood passing therethrough. In the case of magnetically suspended pumps, the electrical signals used to suspend the rotor may also be used to estimate a flow rate of blood passing therethrough. Rotor position sensors may also be employed for such estimations, in addition to other measurements. However, such blood flow estimating algorithms are generally significantly influenced by the viscosity of the blood flowing through the pump. Without a method to determine the viscosity of the blood, the accuracy of these methods is significantly compromised.

Thus, methods for determining or measuring viscosity of fluid passing through a pump device may be of interest. For example, knowledge of a viscosity of a fluid may improve the operation of a pump device. Accordingly, it would be advantageous to provide a system for predicting, estimating, or determining a viscosity of blood that does not require sampling of the fluid passing therethrough.

SUMMARY OF THE INVENTION

One aspect of the present invention relates to a method for determining a viscosity of a fluid passing through a fluid pump. Particularly, in one embodiment, a fluid pump is provided including a rotor exhibiting a first axial setpoint. Further, the rotor is caused to respond to a second axial setpoint from a first axial setpoint and an amount of energy associated with causing the rotor to respond to the second axial setpoint from the first axial setpoint is determined. The amount of energy is correlated with a viscosity of a fluid interacting with the rotor. Thus, the viscosity of the fluid interacting with the rotor is determined. In another method according to the present invention, a fluid pump is provided having a rotor that is initially unsuspended. Further, the rotor is suspended and an amount of energy associated with suspending the rotor is determined. The measured amount of energy is correlated to a viscosity of fluid interacting with the rotor. A further method includes providing a fluid pump having a rotor and suspending the rotor of the fluid pump. Further, subsequent to magnetically suspending a rotor, allowing the rotor to become unsuspended and quantifying an energy response of the rotor to a selected axial setpoint subsequent to allowing the rotor to become unsuspended so as to determine a viscosity of fluid passing through the pump.

Generally, the present invention contemplates a method for determining a viscosity of a fluid interacting with a rotor. Specifically, a fluid pump having a rotor may be provided and the rotor may be non-impellingly moved. Further, an amount of energy associated with non-impellingly moving the rotor, during a selected time period, may be determined. Also, the amount of energy may be correlated with a viscosity of a fluid interacting with the rotor to determine the viscosity of the fluid interacting with the rotor. In another embodiment, a fluid pump having a rotor may be provided and the rotor may be axially moved. Further, an amount of energy associated with axially moving the rotor, during a selected time period, may be determined. Also, the amount of energy may be correlated with a viscosity of a fluid interacting with the rotor to determine the viscosity of the fluid interacting with the rotor.

A further aspect of the present invention relates to a method for determining a viscosity of a fluid interacting with a rotor. Specifically, a rotor of a fluid pump is suspended and, subsequent to suspending the rotor, the rotor is unsuspended. Further, an energy response of the rotor to a selected axial setpoint subsequent to allowing the rotor to become unsuspended is quantified so as to determine a viscosity of fluid passing through the pump.

Another aspect of the present invention relates to systems for determining a viscosity of a fluid. Particularly, in one embodiment, a system for pumping a fluid includes a pump device having a rotor capable of magnetic suspension, the pump configured for impelling fluid flow. Further, the system includes a controller for suspending a rotor according to a control algorithm implemented therewith and a processor operably connected to the controller and configured for estimating a viscosity of fluid within the pump by way of measuring an amount of energy for suspending the rotor during a selected time period. Another system according to the present invention relates to a system for pumping blood of a patient. More specifically, the system includes a pump device including a rotor capable of magnetic suspension by way of an axial magnetic bearing, the pump configured for impelling blood flow within a patient. Also, the system includes a controller for selectively providing a magnitude of electric current to the axial magnetic bearing according to a control algorithm implemented therewith and a processor operably connected to the controller and configured for estimating a viscosity of blood within the pump by way of measuring an amount of energy provided to the axial magnetic bearing during a selected time period.

Features from any of the above mentioned embodiments may be used in combination with one another in accordance with the present invention. In addition, other features and advantages of the present invention will become apparent to those of ordinary skill in the art through consideration of the ensuing description, the accompanying drawings, and the appended claims.

BRIEF DESCRIPTION OF THE DRAWINGS

FIG. 2A shows a graph depicting electrical current supplied to an axial magnetic bearing and axial position of a rotor for a pump device having a fluid therein comprising 10% Glycerol and 90% water;

FIG. 2B shows a graph depicting electrical current supplied to an axial magnetic bearing and axial position of a rotor for a pump device having a fluid therein comprising 40% Glycerol and 60% water;

DETAILED DESCRIPTION OF THE INVENTION

Generally, the present invention relates to a method for estimating or otherwise determining a viscosity of a fluid. For example, a pump device (e.g., a VAD) may be configured such that operation of the pump device may provide a response useful for estimating or otherwise determining a viscosity of a fluid (e.g., blood) passing therethrough or otherwise interacting therewith. Also, while the present invention has been described with respect to a pump device for pumping "fluid," the present invention contemplates that "fluid," as used herein may encompass a liquid, a gas, a slurry, a suspension, a liquid or gas having solids therein, a solution, mixtures of the foregoing, or other generally flowable media. In one example, the present invention contemplates determining viscosity of blood within or being pumped through a pump device having a magnetically suspended rotor in a human by perturbing a axial setpoint (i.e., a desired axial position) of a rotor, analyzing the energy utilized for suspending the rotor, and thus determining a viscosity measurement of blood interacting therewith. "Setpoint," as used herein, means a desired value of a parameter in a control system. As used herein, "setpoint" also encompasses a condition or state where the control system or the source of impetus or power (i.e., an electrical, hydraulic, or mechanical power source) that the control system commands is not energized (i.e., an "off" condition). Further, a "setpoint" may be time invariant or time-varying, without limitation. Thus, a "setpoint," as used herein, encompasses a parameter that is stepwise varying, constant, oscillating, time-varying, or any combinations thereof. In addition, for clarity, "exhibit" or other forms thereof, as used herein in connection with "setpoint" means to generally follow or approximate (within the behavior and dynamics of a system) a desired value of a parameter in a control system. According to the present invention, periodic viscosity measurements may take place with the pump stopped for a short time or may be performed during operation, without limitation. Viscosity information may be useful for estimating blood flow rates through the VAD. As mentioned above, calibration or training of a blood flow estimator as described by the inventors in U.S. patent application Ser. No. 10/225,906 may be performed. However, such calibration may be relatively sensitive with respect to a viscosity of fluid passing through the pump device. Thus, the present invention contemplates that accurate measurement of a flow rate of fluid through a pump device may be dependent on the accuracy of periodic measurements of viscosity of the fluid.

Figure 1A:
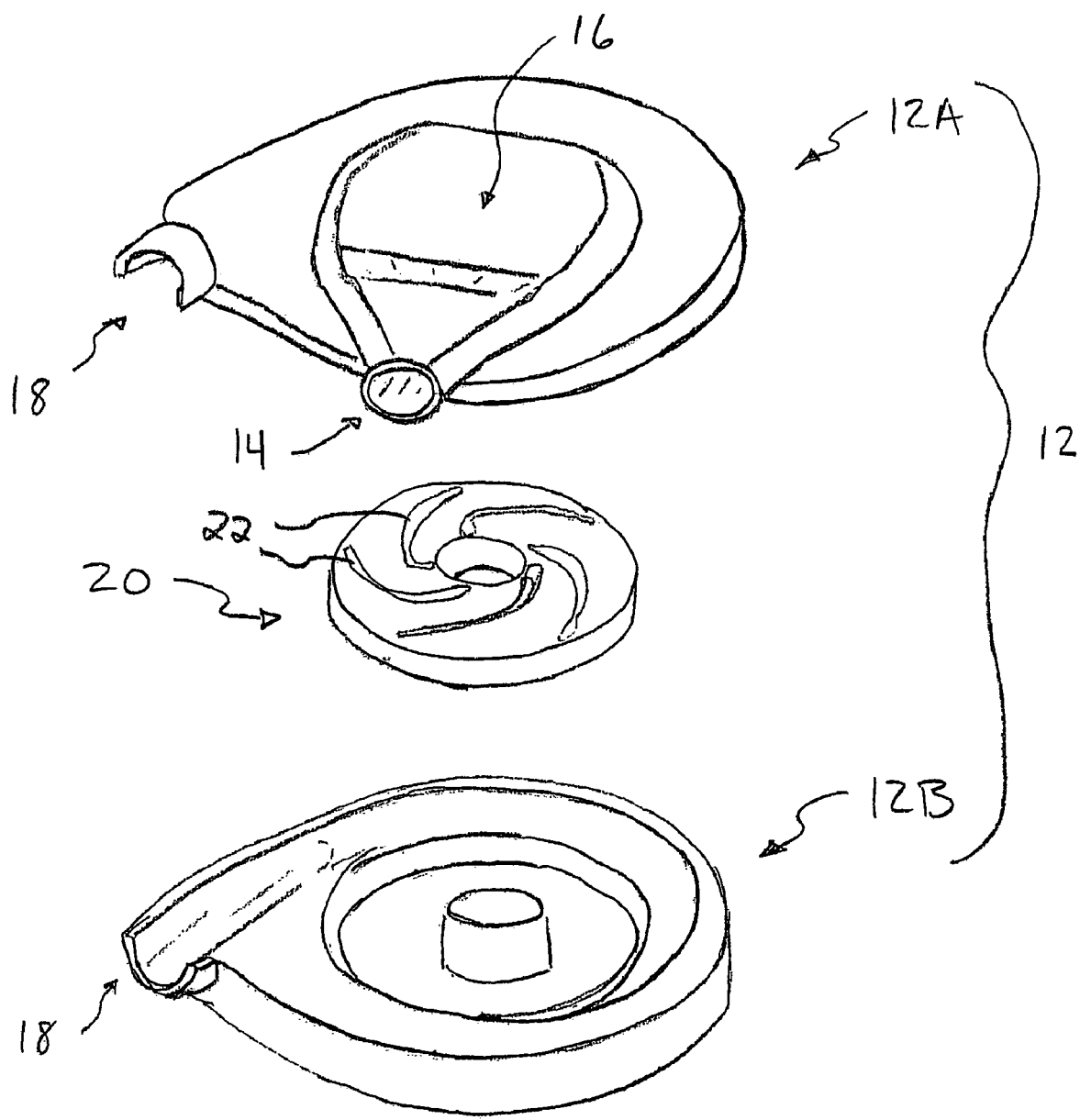
FIG. 1A shows an exploded, perspective view of a pump device including a rotor.

The following described embodiments are to be considered illustrative and not restrictive. As shown in FIG. 1A, one embodiment of a blood pump 10 is shown in an exploded assembly view and includes a housing 12 with an inlet 14, a flow turning structure 16, and an outlet 18. The flow turning structure 16 may be configured to redirect incoming fluid flow in a gentle fashion. The structure 16 may be configured such that flow swirls around in a generally spiral configuration (e.g., a logarithmic spiral), which may equalize the flow rate and pressure entering the inlet 14. Additionally, a generally spiral configuration may reduce flow discontinuities or other disruptions in the flow that may be detrimental to pump efficiency. In addition, as shown in FIG. 1A, blood pump 10 includes upper and lower halves 12A and 12B of the housing 12, and a rotor 20. "Rotor," as used herein, means a device used to influence, by rotation, a fluid to flow in a desired direction or toward a desired flow path. The rotor 20 may be, in some respects, similar to a rotor of a motor, and may include magnetic material (e.g., soft iron magnetic material structures or other permanent magnetic structures) that act as targets on the rotor for magnetic bearing actuators, as known in the art. The rotor 20 may also include a plurality of vanes 22, as shown in FIG. 1A. The housing 12 may be structured for providing curved or straight fluid gaps proximate the rotor 20. The gaps may be structured for, in conjunction with the rotor 20, accommodating flow without damaging blood or other sensitive fluids. For example, gaps may be relatively short in length, yet with large bending radii to allow gentle backflow around the rotor 20. Thus, during rotation of rotor 20, vanes 22 may impel sensitive fluid (e.g., blood) from the inlet 14 into a volute, which is formed around a perimeter of an inner space of the housing 12. The volute may be formed in generally spiral shape (e.g., a logarithmic spiral), positioned about the center of the pump 10. Thus, the volute may gather flow from the vanes 22 and direct such flow toward the outlet 18.

Figure 1B:
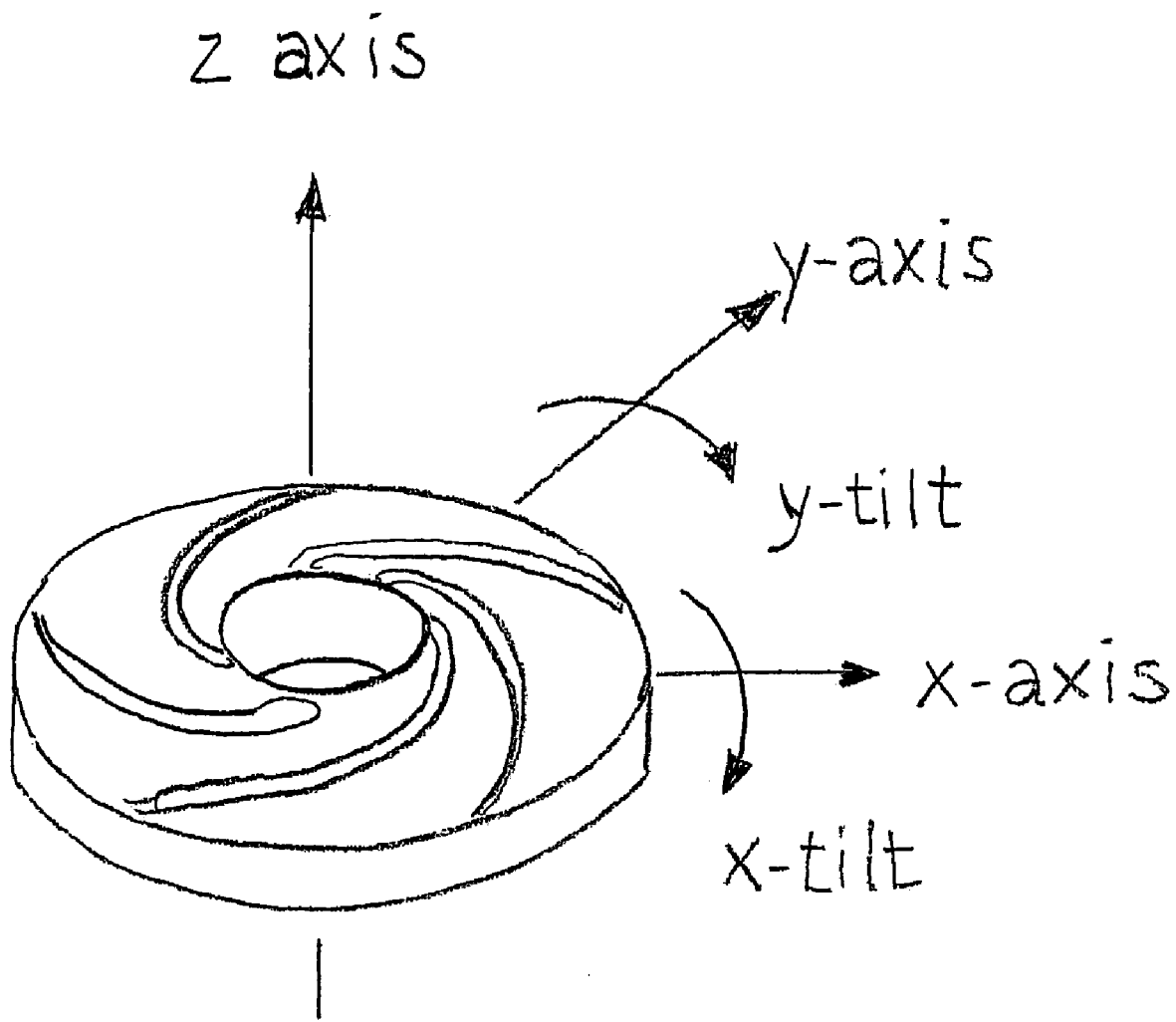
FIG. 1B shows a perspective view of the rotor of the pump device as shown in FIG. 1A.
Figure 1C:
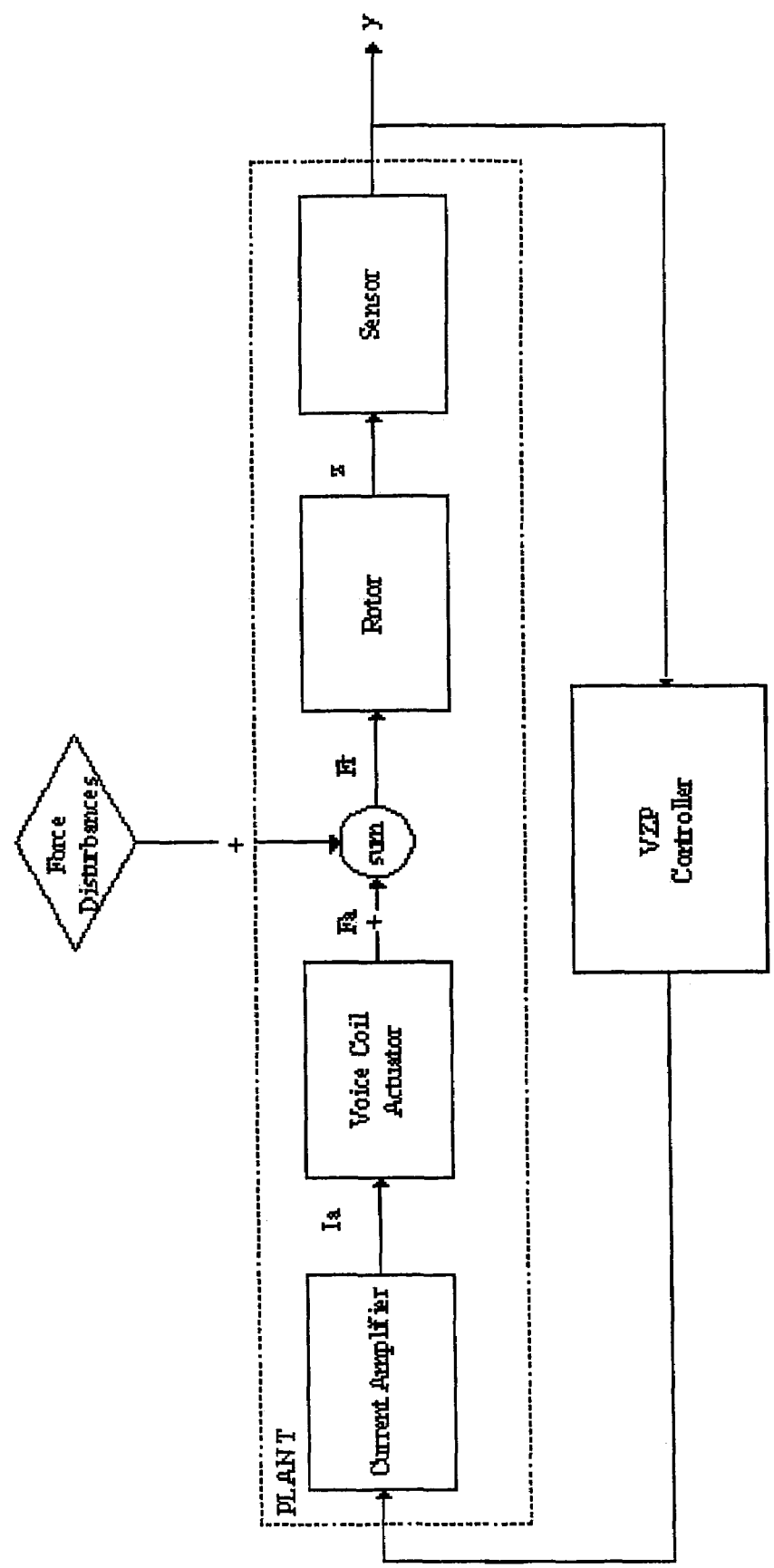
FIG. 1C shows a schematic diagram of system including a VZP control system.

As known in the art, blood pump 10 may further include permanent magnetic structures for forming a passive radial bearing and permanent magnet structures for forming a passive moment bearing. Also, blood pump may include an electromagnetic axial bearing comprising an active thrust coil and a permanent magnet. Further, blood pump 10 may include an electromagnetic motor having a motor winding and motor permanent magnet. FIG. 1B shows x-axis, y-axis, z-axis, y-tilt, and z-tilt for a rotor 20 as shown in FIG. 1A. As used herein "axial" may generally refer to the z-axis as shown in FIG. 1B. Such degrees of freedom may be of interest during suspension and rotation of rotor 20. Accordingly, by way of magnetic suspension and magnetic bearings, also as known in the art, a rotor 20 may be suspended by and propelled by magnetic fields that are determined by way of an automatic control system. For example, one such a control system is shown schematically in FIG. 1C and includes a so-called virtual zero power ("VZP") control algorithm. VZP control algorithms are known in the art. For example, U.S. Pat. Nos. 6,227,817 and 6,244,835, each of the disclosure of which is incorporated in its entirety by reference herein, discloses and refers to various VZP control algorithms. However while a VZP control algorithm is depicted in FIG. 3, it should be understood that there are many possible feedback control algorithms that may be employed for controlling the rotor. Such algorithms include proportional-integral-derivative (PID) or any suitable automatic control algorithm known to or developed by those of skill in the art of magnetic bearing control may be employed, without limitation.

Generally, the present invention contemplates that an amount of energy utilized in controlling a rotor during movement thereof may be correlated to a viscosity of the fluid interacting therewith. However, a direct measurement of the energy imparted to the rotor may require additional sensors or knowledge of flow characteristics of the fluid. Therefore, the present invention contemplates that an amount of energy applied to a rotor of a pump device such as a VAD and under automatic control may be employed for indicating (e.g., correlated to) a viscosity of a fluid passing therethrough or otherwise interacting with the rotor. Generally, the energy imparted to a rotor of a pump device may be approximated by measuring the energy supplied to an axial magnetic bearing for suspending the rotor during operation of the pump device. Summarizing, the present invention contemplates that a rotor may exhibit a first axial setpoint and the rotor may be caused to respond to a second axial setpoint from the first axial setpoint. An energy associated with the response of the rotor to the second axial setpoint may be determined and a viscosity of a fluid interacting with the rotor may be determined via correlation. Put another way, more generally, the present invention contemplates that a rotor of a fluid pump may be axially moved and an amount of energy associated with axially moving the rotor may be determined. Further, the amount of energy may be correlated with a viscosity of a fluid interacting with the rotor to determine the viscosity of the fluid interacting with the rotor.

In one embodiment, the rotor may be initially unsuspended. "Unsuspended," as used herein, means that an axial magnetic bearing is not operated under "active" or automatic control (i.e., via a feedback control system). Further, "suspended," as used herein, means that the axial magnetic bearing is operated under active" or automatic control. It should be understood that "suspended" encompasses operation of the axial magnetic bearing employing a controller that implements a VZP algorithm (wherein current in the magnetic bearing may become, at times, very low or even zero) or another algorithm as may be desired. Thus, an operational mode of the axial magnetic bearing may affect whether the rotor is suspended or unsuspended. It should be recognized that a natural heartbeat or movement of a patient may cause movement of a rotor despite the rotor being "unsuspended." Further, a rotor may be rotating without being suspended. As the rotor "lifts off," (e.g., from an unsuspended equilibrium state such as, for instance, contacting a surface of a cavity within which the rotor resides) becomes suspended, and may begin to rotate, the rotor is propelled by magnetic fields according to the forces thereon. Thus, a response of the rotor may be measured or monitored as lift off and stabilization of the rotor occurs. For example, an axial position of the rotor as a function of time may be measured or monitored using a rotor position sensor (e.g., an eddy current sensor, variable reluctance type, acoustic, infrared reflectance type, or any sufficiently reliable non-contact position sensor). Such position measurement may be employed during automatic control of the active z-axis of the rotor during magnetic suspension thereof.

Put another way, the present invention contemplates that energy supplied or expended for suspending (i.e., energy supplied to the axial magnetic bearing) a rotor under automatic control to a selected input (e.g., a change in a desired axial setpoint) may be observed and correlated to at least one characteristic of the environment experienced by the rotor. More specifically, according to the present invention, an amount of energy (i.e., effort or impetus) utilized for influencing a rotor during a selected operational regime of the rotor may be measured and correlated to the viscosity of the fluid passing through the pump device. In one embodiment, the cumulative energy for causing a rotor which is initially at rest to exhibit a selected operational parameter may be measured and related to a viscosity of a fluid passing through a pump device. In another embodiment, the cumulative energy for causing a rotor to exhibit a selected stabilization behavior may be measured and related to a viscosity of a fluid passing through the pump device.

Electrical energy may be determined by the following equation:

$$\int (Vi) dt$$

Where:
V is voltage (as a function of time); and
i is current (as a function of time).

In one example, FIG. 2A shows a plot of measured current in the axial magnetic bearing (i.e., axial thrust coil) and axial rotor position of a VAD for a rotor starting at axial setpoint (i.e., axial position) $P_0$ and transitioning to axial setpoint (i.e., axial position) $P_1$, wherein the fluid passing through the VAD is a mixture of 10% glycerol and 90% water. Axial position as shown in FIG. 2A is shown relative to an arbitrary reference plane positioned at an uppermost (i.e., away from magnetic bearing) axial position. In one example, a positive rotor position may correspond with a position that is furthest away from the pump inlet (e.g., an axial position associated with inlet 14 as shown in FIG. 1A). Thus, axial setpoint $P_1$ may correspond to an decrease in distance (i.e., axial movement of a rotor toward the pump inlet) from the arbitrary reference plane and an associated response of electrical current to the axial magnetic bearing. More specifically, at substantially time $t_0$, an axial setpoint (of the controller) is changed from $P_0$ to $P_1$. In response, the controller may determine or otherwise cause current to be supplied to the axial magnetic bearing according to the control algorithm implemented therewith, as is shown in FIG. 2A. Such current (as a function of time) may cause the position of the rotor to change as a function of time, which is also shown in FIG. 2A. The position of the rotor may pass a crossover point labeled "C" and may overshoot the selected axial setpoint of $P_1$ by a maximum magnitude of $x_0$. Further, a position of the rotor may approach or settle within $\pm \Delta x$ of $P_1$ (i.e., a selected difference between a position of rotor and the selected axial setpoint $P_1$) subsequent to crossover C (i.e., overshooting the selected axial setpoint $P_1$).

Thus, the present invention generally contemplates that an amount of energy utilized for influencing or controlling an axial position of a rotor may be determined for a selected portion of the response of the rotor. Specifically, assuming that the voltage is constant (or otherwise measured) the product of the voltage applied to the axial magnetic bearing and the current passing therethrough may be integrated with respect to time to determine an amount of energy supplied to the axial magnetic bearing. In one embodiment, the energy supplied to the rotor may be determined for the time period between $t_0$ and another time subsequent thereto wherein $\Delta x$ is less than or equal to about 5% of the selected axial setpoint $P_1$. Utilizing a measurement of energy supplied to the rotor so as to correlate or otherwise determine a viscosity of a liquid passing through a pump device may be advantageous, because such a measurement may be substantially independent of the particular control algorithm employed or the overall power capability of a system available for such a controller algorithm. Thus, once a method or apparatus of the present invention has been calibrated (empirically or otherwise) to one or more fluids with known viscosities, respectively, it may not require further calibration, even if a control algorithm is changed or the power capability of the system changes.

In addition, the present invention contemplates that utilizing an energy measurement for determining a viscosity of a fluid passing through a pump may be performed for one or more operational regime of the rotor. For example, a magnitude of energy applied for controlling the rotor may be measured between $t_0$ and a time ($t_c$) associated with crossover point C of the position of the rotor. In another example, a magnitude of energy applied for influencing the rotor may be measured between $t_0$ and a time ($t_x$) associated with a maximum overshoot $X_0$ of the position of the rotor. In a further example, a magnitude of energy applied to the rotor may be measured between $t_0$ and a time ($t_s$) associated with the position of rotor being within $\pm \Delta x$ (e.g., within 5% of setpoint $P_1$). Further examples may include measuring a magnitude of energy applied for influencing the rotor measured between times $t_c$ and $t_x$, times $t_x$ and $t_s$, or between any two of the following: $t_0$, $t_c$, $t_x$, and $t_s$.

Of course, the foregoing examples are not limiting. More generally, an amount of energy may be measured for any selected time interval during which a transition (e.g., a response) from a first axial setpoint of the rotor to a second axial setpoint of the rotor, under automatic control, occurs without limitation. By way of example, a second setpoint may cause the rotor to move in an axial direction (i.e., relative to an arbitrary reference plane) that is generally opposite to the axial direction that a rotor moves in response to a change in axial setpoint from $P_0$ to $P_1$. Accordingly, axial magnetic bearing current may, therefore, initially be reduced and then be increased (i.e., generally opposite of the current behavior as a function of time shown in FIGS. 2A and 2B). Further, although it may be advantageous to control the axial position of a rotor under automatic control, the present invention contemplates that control may be accomplished via more simplified control mechanisms or algorithms, as known in the art, if desired.

For comparison, FIG. 2B shows a plot of measured axial magnetic bearing current in the axial magnetic bearing and rotor position of a VAD for a rotor starting at an axial position corresponding to axial setpoint P0 and transitioning to an axial position corresponding to axial setpoint P1, wherein the fluid passing through the VAD is a mixture of 40% glycerol and 60% water. As described with respect to FIG. 2A, at substantially time t0, a axial setpoint (of the controller) is changed from P0 to P1. In response, the current in the axial magnetic bearing may be varied according to the control algorithm implemented by a control system and the position of the rotor may respond accordingly, Particularly, as shown in FIG. 2B, may pass a crossover point labeled "C" and may overshoot the selected axial setpoint of P1 by a maximum magnitude of x0. Further, an axial position of the rotor may approach or settle within ±Δx (i.e., a selected difference between a position of rotor and the selected axial setpoint P1) subsequent to overshooting the selected axial setpoint P1.

The present invention contemplates that an initial position of a rotor with which a viscosity measurement may be performed may be a resting state. Thus, current in an axial magnetic bearing may initially be zero. As known in the art, an axial magnetic bearing or actuator (i.e., a coil) may be positioned around a circumference of the rotor and may be configured to generate axial force (e.g., a Lorentz force) in either direction depending on the polarity of the current. Thus, a negative current as may be indicated if a current in an axial magnetic bearing is zero shown in FIGS. 2A and 2B indicates that the current is reversed in polarity as compared to a positive current.

Figure 3A:
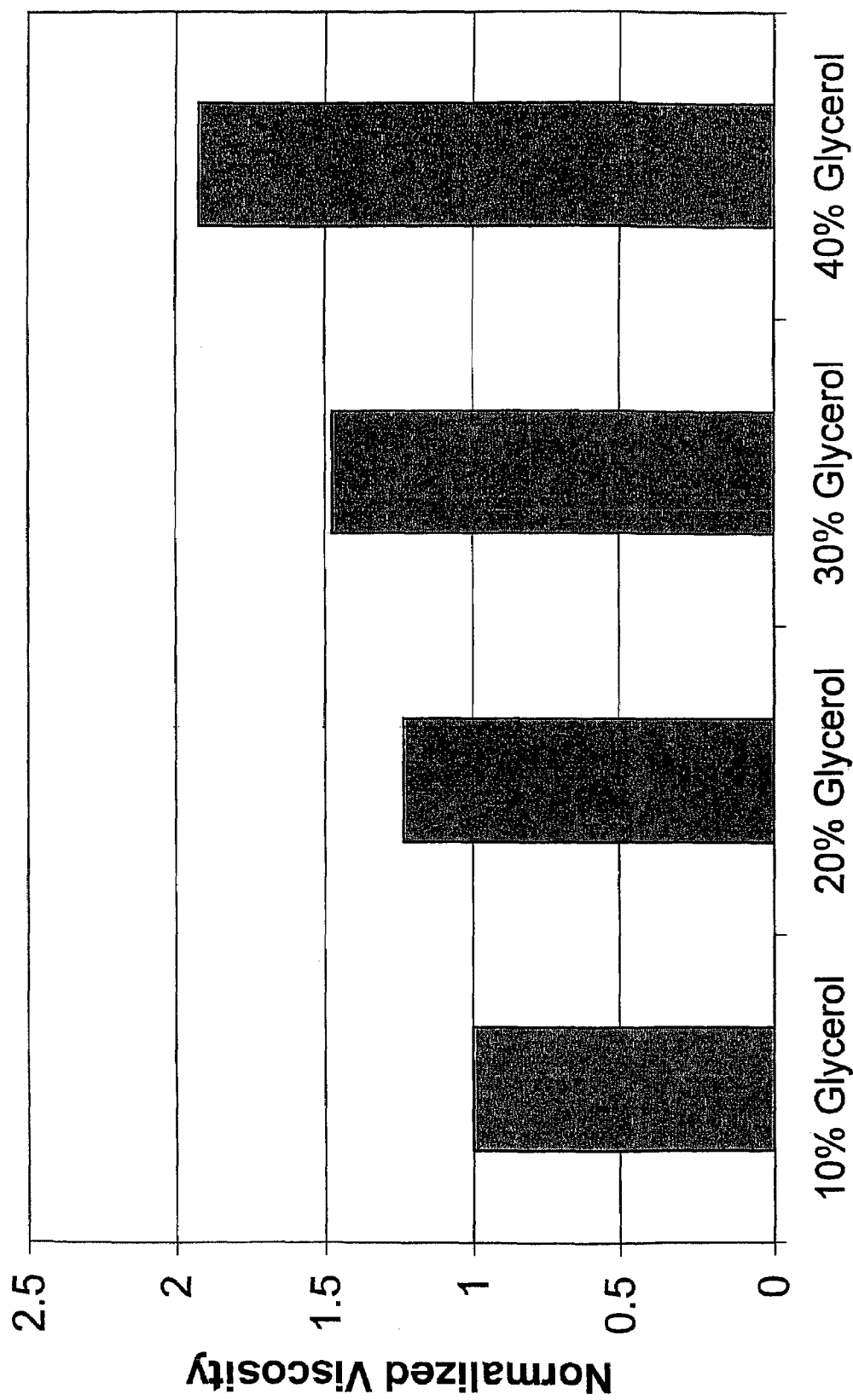
FIG. 3A shows a graph depicting normalized viscosity (determined from an amount of energy to suspend a rotor from rest) as a function of glycerol percentage of a water and glycerol solution.
Figure 3B:
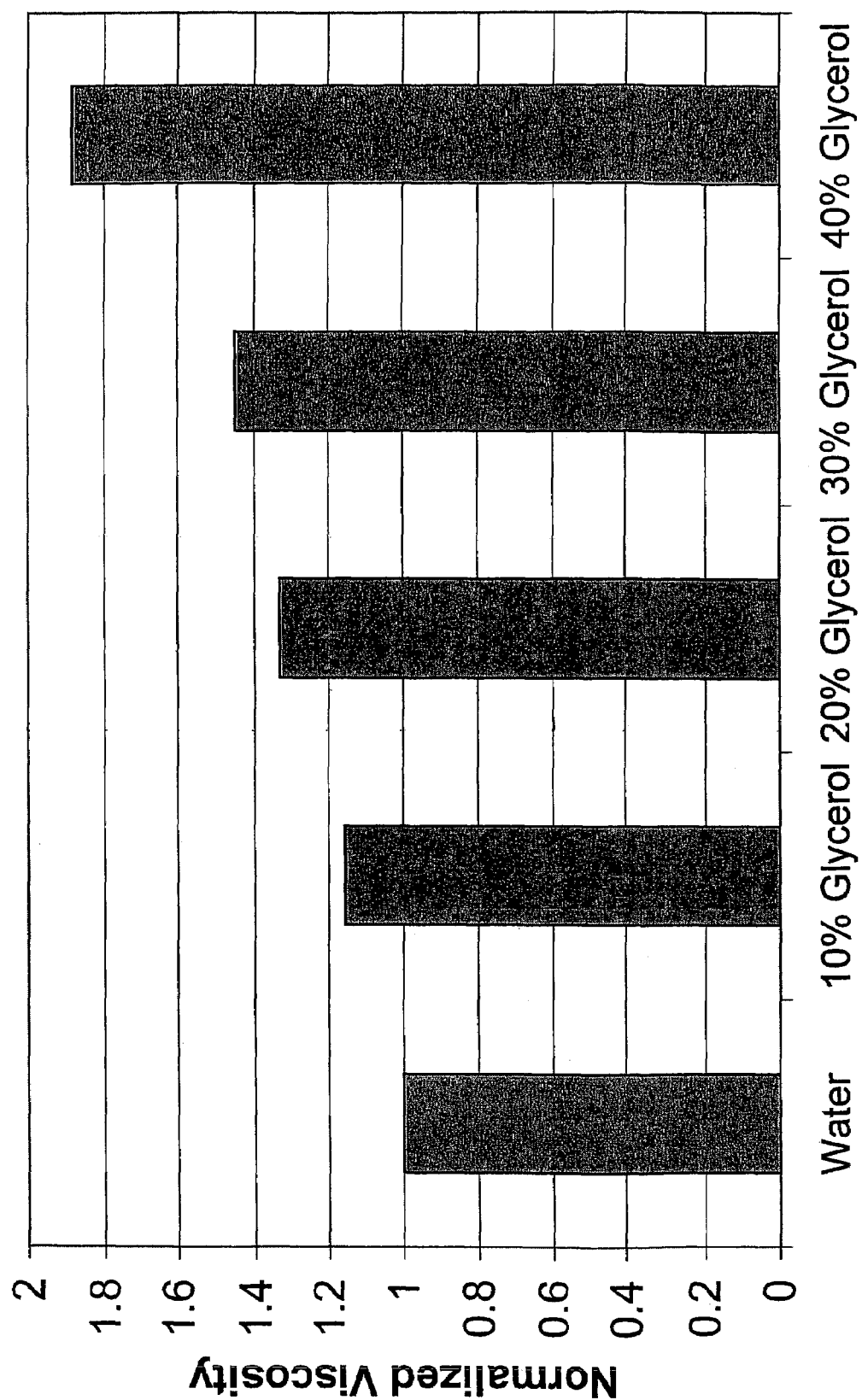
FIG. 3B shows a graph depicting normalized viscosity (determined in relation to an amount of energy for the rotor to exhibit ±5% of a second axial setpoint) as a function of glycerol percentage of a water and glycerol solution.

FIG. 3A shows normalized viscosity measurements derived from respective axial magnetic bearing current waveforms (e.g., as shown in FIGS. 2A and 2B) for four different glycerol and water solutions, wherein a first position of a rotor is a position of rest. Particularly, normalized viscosities for solutions including 10% glycerol and 90% water, 20% glycerol and 80% water, 30% glycerol and 70% water, and 40% glycerol and 60% water are shown in FIG. 3A. More particularly, the normalized viscosities shown in FIG. 3A are representative of the total energy required to move a rotor from an unsuspended state to a suspended state (e.g., from $t_0$ to $t_c$, as shown in FIGS. 2A and 2B). Also, FIG. 3B shows normalized viscosity measurements derived from respective axial magnetic bearing current waveforms (e.g., as shown in FIGS. 2A and 2B) for the same four different glycerol and water solutions listed in FIG. 3A and representative of the total energy required to move a rotor from an unsuspended (non-rotating or rotating) state to a suspended (non-rotating or rotating) state within about 5% of the selected axial setpoint $P_1$ (e.g., from $t_0$ to $t_s$, as shown in FIGS. 2A and 2B).

Summarizing, the present invention contemplates that a pump having a magnetically suspended rotor may be operated so as to determine or indicate a viscosity of a fluid passing therethrough. In one embodiment, a rotor of a pump may be initially stationary and may be influenced by way of automatic control (i.e., feedback control) to exhibit or follow a selected setpoint. Such a stationary condition of a rotor of a pump device may occur subsequent to normal operation of the pump without substantial disruption in the function thereof. Thus, a pump may be operated under desired conditions and then may be de-energized so that the rotor may become unsuspended and, optionally, may come to a resting state. Then, a selected axial setpoint for determining a viscosity of a fluid passing through the pump may be provided to the feedback control system and an energy measurement of the energy provided to the rotor may be performed. In another embodiment, as discussed above, an axial position of a rotor of a pump device may change (i.e., respond) from a first axial setpoint to a second axial setpoint and an energy measurement of the energy utilized for causing the response of the rotor may be performed.

From the foregoing discussion, it may be appreciated that the energy applied to an axial magnetic bearing may be used as an approximation for an amount of energy that is utilized for causing a rotor response with respect to a change of an axial setpoint of the rotor. In addition, losses of energy (unrelated to viscosity of a fluid passing through the pump) may be calculated or may be otherwise known and may be corrected for in correlating an amount of energy to a viscosity of fluid, if so desired. Generally, it may be advantageous to subtract energy losses (e.g., electrical heating, mechanical friction, etc.) from a determination of energy applied to a rotor so that the corrected energy amount is more closely related to the viscosity of the fluid. Further, it may be advantageous to account for (e.g., subtract) kinetic energy of the rotor in determining an amount of energy applied to a rotor. Such energy considerations may more accurately estimate or determine the amount of energy associated with rotor interaction with a fluid within a pump device. Accordingly, consideration of losses or energy that is not associated with "work" or energy applied to a rotor may provide an increased accuracy in determining a viscosity of the fluid passing through a pump. Similarly, energy that may be expended in relation to phenomena or behavior not related to viscosity may be accounted for or considered relative to an energy determination for correlation to a viscosity of a fluid passing through the fluid pump.

Figure 4:
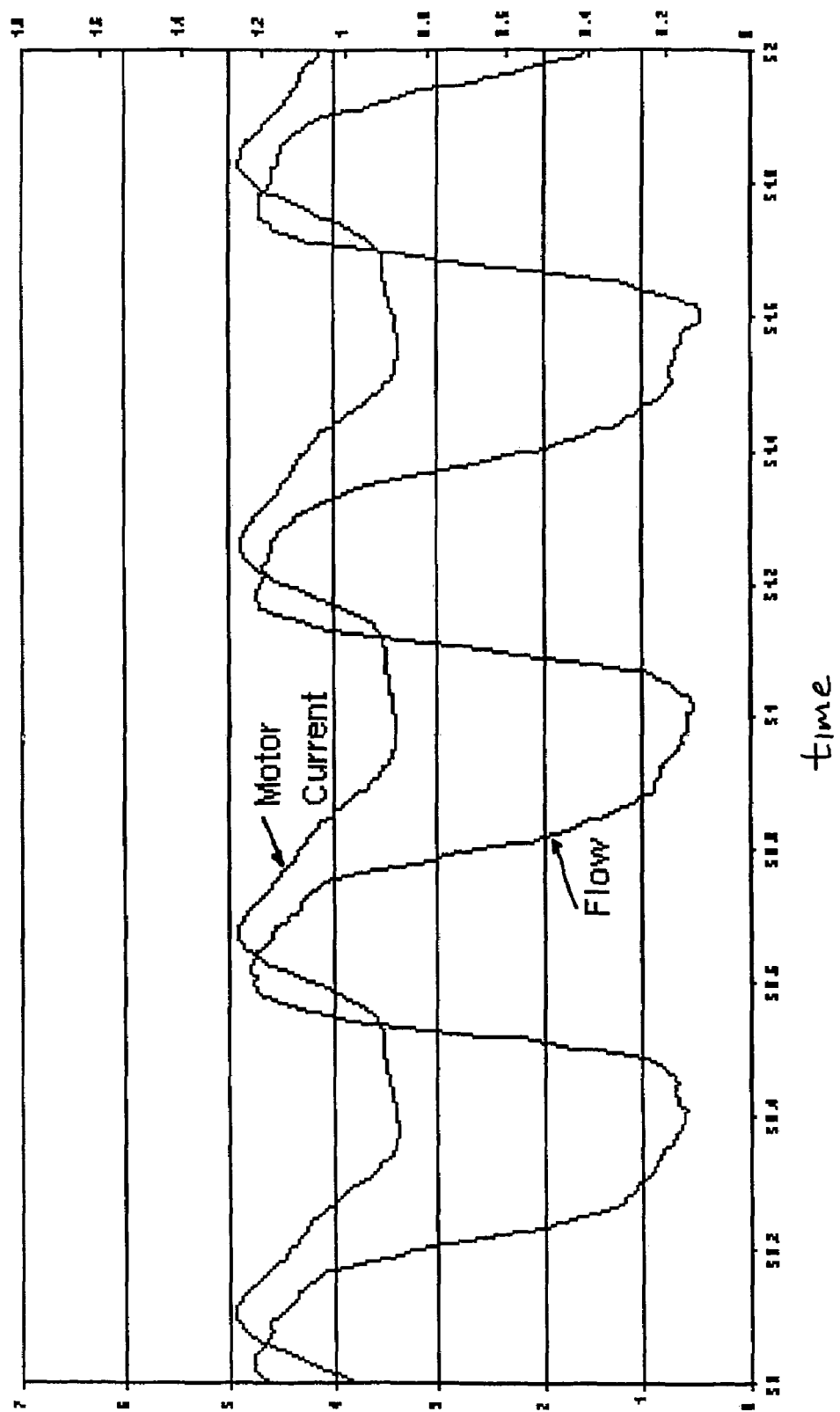
FIG. 4 shows a graph depicting motor current and flow for a rotor system under the influence of a natural heartbeat.

In another aspect of the present invention, a viscosity measurement method may account for (i.e., subtract out or otherwise consider) energy related to pulsing due to a heart beat in determining, indicating, or measuring the energy required to suspend the rotor from a first axial setpoint (from rest or otherwise) to a second axial setpoint. Particularly, aspects of the methods for determining a viscosity of a fluid passing through a pump device may be selected, timed, or configured to minimize noise, interference, or influence of a natural heartbeat with respect to measurements of rotor position or energy supplied to the axial magnetic bearing for suspending a rotor. As known in the art, a pump device (e.g., a VAD) for assisting a natural heart may be influenced by operation of the natural heart, namely the influence of the heart beating to impel blood through the body of the patient. Specifically, FIG. 4 shows a graph illustrating flow rate as a function of time and current to the rotation motor as a function of time. As may be evident from FIG. 4, a minimum load (i.e., external force) across the rotor may occur when the natural heart is in the systolic phase (ejecting blood). In another aspect of the present invention, an energy measurement may be performed so as to minimize the influence of a natural heartbeat on the energy measurement. For example, according to the present invention, the methods and measurement of the energy for suspending the rotor, as described above, may generally commence or initiate with the beginning of the systolic phase, so that there should be a minimum of interference. In another embodiment, an amount of energy for suspending a rotor may be measured and the amount of energy that relates to the cardiac cycle of a natural heartbeat may be subtracted so as to more accurately quantify the amount of energy applied to the rotor. Such an energy correction could be determined by a non-invasive measurement of blood pressure by the pump operator or by the pump controller.

From the foregoing discussion, in general, it may be appreciated that operation of a VAD and measurement of the energy supplied to a magnetic axial bearing for generating axial force on the rotor may be utilized to determine a viscosity of the fluid passing through the VAD. More particularly, it may be appreciated that the cumulative energy applied to the axial magnetic bearing may be correlated to a viscosity of the fluid interacting with the rotor. Thus, in one embodiment, a time for the rotor to move from rest to approximately a selected axial position (i.e., in response to an input) may be obtained, along with the current in the axial magnetic bearing that generates axial force. The time and overall effort of the controller may thus be determined and may be compared to values that have been previously obtained with respect to operation of the pump when filled with fluids of various, known viscosities. Summarizing, one method according to the present invention may include providing a fluid pump having a rotor and axially moving the rotor. Further actions include determining an amount of energy associated with axially moving the rotor during a selected time period and correlating the amount of energy with a viscosity of a fluid interacting with the rotor to determine the viscosity of the fluid interacting with the rotor.

In another aspect of the present invention, the present invention contemplates that an energy measurement and viscosity correlation may be performed in relation to movement of a rotor in a direction corresponding any degree of freedom that does not cause substantial fluid flow through the pump device. For example, lateral motion (e.g., along the x-axis, y-axis, or z-axis), tilt (e.g., x-tilt or y-tilt), or combinations thereof not cause substantial fluid flow through the pump device. Further, such motion may be employed for the purpose of performing an energy calculation (for a selected time period) and subsequent correlation to viscosity of a fluid interacting with a rotor. Explaining further, the present invention contemplates that motion of the rotor may occur without causing substantial fluid flow through the pump. Accordingly, the term "non-impelling motion" or "non-impellingly moving" as used herein, means to move the rotor but not substantially impel fluid through the pump device. Such non-impelling motion of a rotor may be advantageous for performing a viscosity measurement, because energy for causing non-impelling motion of the rotor may more directly relate to the viscosity of a fluid interacting therewith, since energy consumed to impel fluid through the pump may be minimized or deemphasized.

For example, any of the above-described methods may be practiced with respect to energy related to non-impelling motion of a rotor. In one embodiment, a rotor of a pump may be initially not moving and may be influenced by way of automatic control (i.e., feedback control) to non-impellingly move the rotor. Such non-impelling motion of a rotor of a pump device may occur subsequent to normal operation of the pump without substantial disruption in the function thereof. Thus, a pump may be operated under desired conditions and then may be de-energized so that the rotor, optionally, may come to a resting state. Then, an energy measurement of the energy utilized for causing the non-impelling motion of the rotor may be performed. Thus, an amount of energy to cause non-impelling motion of a rotor may be correlated with a blood viscosity.

In another aspect of the present invention, it should also be understood that an energy calculation and subsequent correlation to viscosity of a fluid interacting with a rotor may be performed with respect to a rotational parameter of a rotor. For example, any of the above-described methods relating to an axial position may also be practiced with respect to energy for rotating a rotor. In one embodiment, a rotor of a pump may be initially not rotating and may be influenced by way of automatic control (i.e., feedback control) to follow a selected rotation speed or rotational position setpoint. Such a nonrotating condition of a rotor of a pump device may occur subsequent to normal operation of the pump without substantial disruption in the function thereof. Thus, a pump may be operated under desired conditions and then may be de-energized so that the rotor (substantially) does not rotate and, optionally, may come to a rotationally resting state. Then, a selected setpoint related to rotation (e.g., rotational speed or position) may be provided and an energy measurement of the energy provided to the rotor may be performed. In another embodiment, a rotational condition of a rotor of a pump device may change (i.e., respond) from a first rotational setpoint to a second rotational setpoint and an energy measurement of the energy utilized for causing the response of the rotor may be performed. Thus, an amount of energy for axially, non-impellingly, or rotationally moving a rotor may be correlated with a blood viscosity. Of course, combinations of such energy (with respect to axial, non-impelling, or rotating motion) may be employed in combination for determining a viscosity of a fluid interacting with a rotor of a pump. Particularly, a blood viscosity may be used to enhance the accuracy of a blood flow estimator used by the pump's control electronics.

In another aspect of the present invention, the time it takes for the rotor to become stationary (i.e., from a suspended state to an unsuspended state) may be influenced by blood viscosity. This "settling time" can be characterized and correlated to blood viscosity. In a magnetically suspended rotary pump, in order for the rotor to settle to a selected surface (e.g., a top surface or a bottom surface) of the rotor cavity, the blood would have to flow into or out of the thin gap below the rotor (i.e., a so-called "backgap"). Thus, a settling time associated with an initial, selected axial setpoint may be related to and correlated with the viscosity of blood within the rotary pump. Explaining further, a first axial setpoint may be exhibited by the rotor and then the current in the axial magnetic bearing may be reduced. Further, a settling time may be measured and correlated to a viscosity of fluid interacting with the rotor.

In an additional aspect of the present invention, a viscosity determined by a method or system of the present invention may be employed to indicate the presence of an obstruction or foreign object within the pumping chamber of a pump device. More particularly, a method according to the present invention may indicate the presence of an obstruction (e.g., a solid or at least semisolid object) inside the pump or within the fluid communication path thereof. For example, a blood clot upstream of, downstream of, or within a pump device may effectively interfere with blood flowing through the blood pump. Thus, a viscosity measurement (i.e., correlation) according to a method of the present invention that is performed may indicate a viscosity that is relatively high or even exceeding a typical upper limit. For example, if the patient develops a blood clot and it lodges around or otherwise interferes with the operation of the rotor or flow of blood through the pump, a viscosity measurement during such event(s) may indicate a relatively high or abnormally high viscosity. Further, such a high viscosity determination may be correlated to an obstruction in fluid communication with the pump device. Further, other indicia may be observed so as to determine the presence of an obstruction in fluid communication with a pump device. For example, an axial position of a rotor may be observed and may corroborate or indicate the presence of an obstruction within a pump device. More particularly, an obstruction (e.g, a blood clot, a small piece of tissue, or surgical materials) may be positioned within a pump device and may be positioned between the rotor and the housing of the pump device. Accordingly, movement (e.g., axial, non-impelling, or rotational, etc.) of the rotor in combination with an observed resistance to such movement (via observing a position of the rotor), may indicate an obstruction within the pump device. For example, an axial setpoint may be selected, but the rotor is unable to substantially attain the axial setpoint. Such a situation may indicate physical resistance to axial movement of the rotor within the pump device, which may indicate the presence of an obstruction. Of course, such axial movement behavior may, in itself, indicate the presence of an obstruction in fluid communication with a fluid pump. Thus, summarizing, the present invention contemplates that a relatively high viscosity measurement may indicate the presence of an obstruction in fluid communication with a fluid pump. Optionally, motion of the rotor may be observed and may, in combination with at least one viscosity measurement or alone, may indicate the presence of an obstruction in fluid communication with a fluid pump. The ability to indicate a presence of an obstruction in fluid communication with a pump device may be highly desirable.

In a further aspect of the present invention, a response of a rotor system to an input may be used to determine other characteristics of the rotor system. For example, rotor position may be used to measure the dynamic and axial static stiffness of the suspension system. The axial static stiffness may be measured by observing the rotor position when the z-axis is oriented generally vertically upwardly (i.e., generally opposite to an earthly gravitational force) and comparing the rotor position when the z-axis is oriented generally vertically downwardly (generally aligned with an earthly gravitational force). The external force acting on the rotor may be conceptually (neglecting any other forces) described by the change in the direction of the force of earthly gravitation (i.e., earthly gravitational force upward compared to earthly gravitational force downward equals a change of 2*(the earthly gravitational force on the rotor). Thus, the change in rotor position divided by the force applied (2*(the force of earthly gravity on the rotor)) gives a static stiffness quantification of the rotor system in a direction along the z-axis (FIG. 1B). In addition, the present invention contemplates that an actual damping coefficient may be determined by operating the rotor system without fluid in contact therewith.

Also, natural frequency of the rotor, $\omega_n$, may be determined by:

$$\omega_n = \sqrt{\frac{k}{m}}$$

where:
k is the static stiffness of the axial bearing; and
m is the mass of the rotor.

Other examples of parameters and equations that may be determined (assuming a second order dynamic system) or may be utilized include the critical damping coefficient $c_c$, actual damping coefficient $c_v$, the damping ratio $\zeta$ (zeta), and the damped vibration frequency $\omega_d$ by way of solving, in various fashions, the following equations:

$$c_c = 2m\sqrt{\frac{k}{m}} = 2m\omega_n$$

$$\zeta = \frac{c_v}{c_c}$$

$$\omega_d = \sqrt{1-\zeta^2}\,\omega_n$$

where k is the stiffness of the system and m is the suspended mass.

Figure 5A:
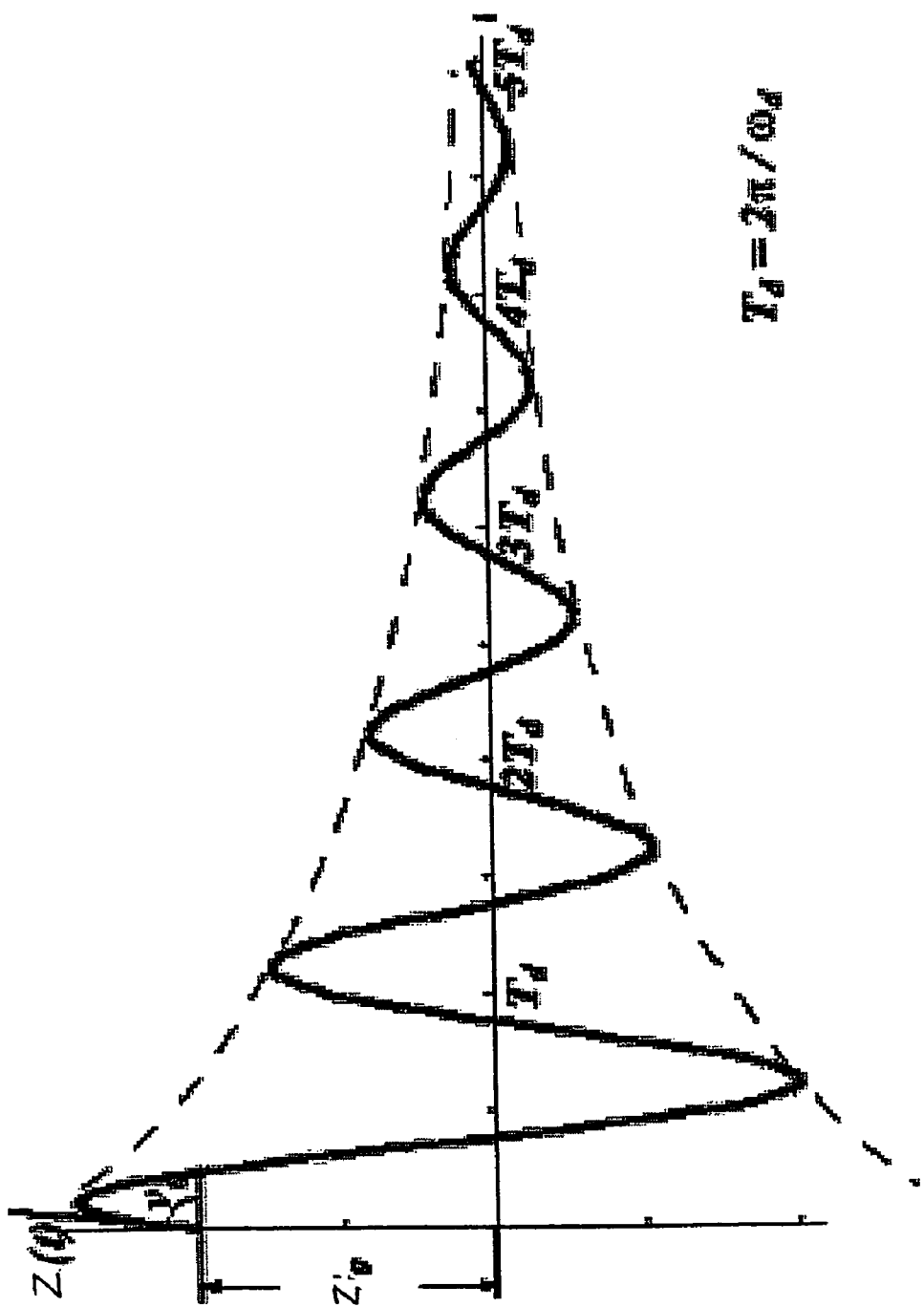
FIG. 5A shows a representation of axial position of a rotor as a function of time for a rotor system which is underdamped.
Figure 5B:
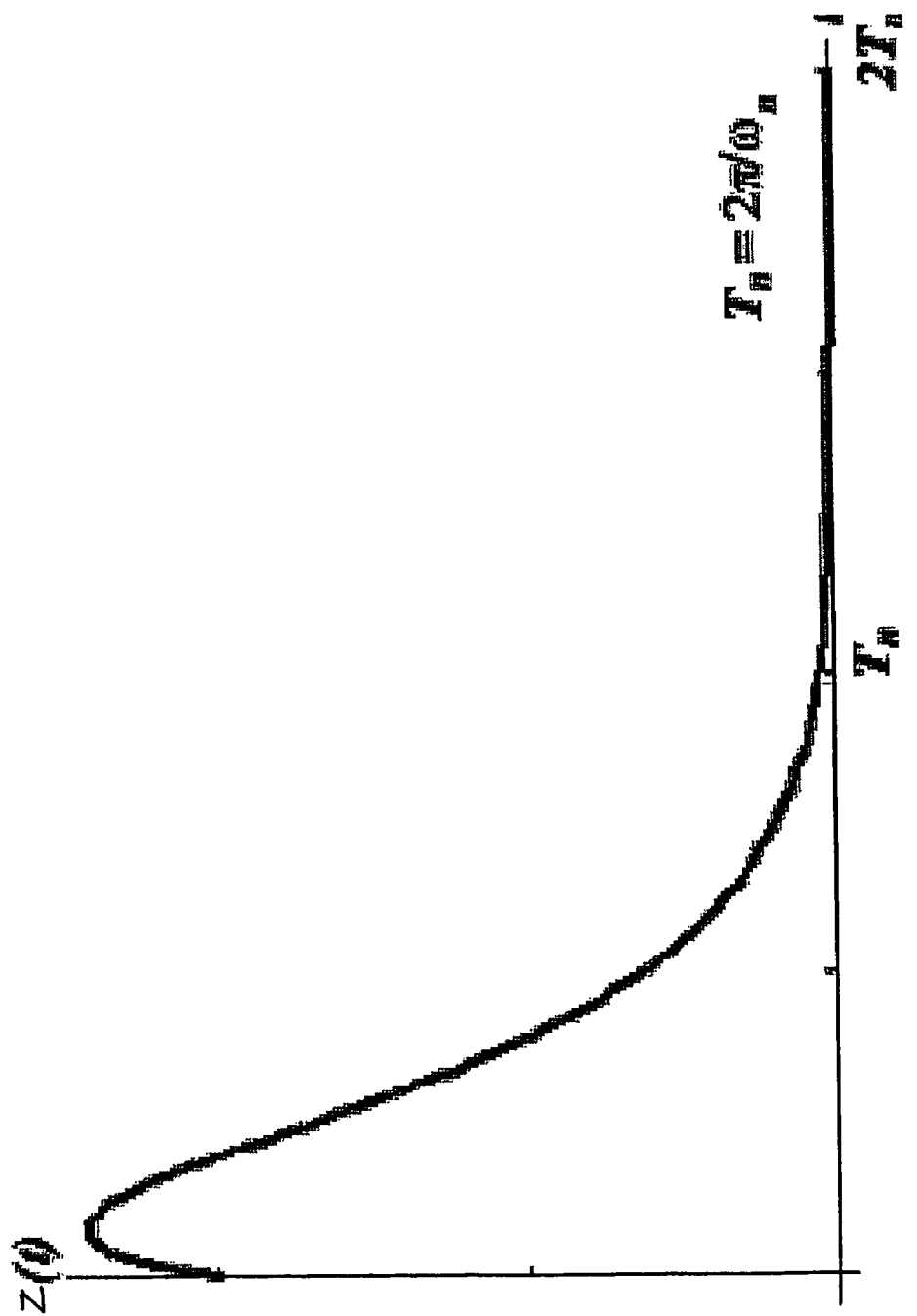
FIG. 5B shows a representation of axial position of a rotor as a function of time for a rotor system which is critically damped.

Thus, in a further aspect of the present invention, measuring rotor position (as a function of time or otherwise) may allow for determination or measurement of: a natural frequency of the rotor system, a damped natural frequency of the rotor system, a damping ratio ($\xi$), a dynamic stiffness, or other characteristics of the rotor environment. Explaining further, a damping ratio of a rotor system may depend largely on the viscosity of the fluid (blood) in which the rotor resides. A fluid with a relatively low viscosity may provide relatively little damping. FIG. 5A shows a representation of axial position of a rotor as a function of time for a rotor system which is underdamped. Contrastingly, a more viscous fluid may provide relatively ample damping. Thus, a rotor may settle in response to an input to a new position in fewer oscillation cycles. FIG. 5B shows a representation of axial position of a rotor as a function of time for a rotor system which is critically damped system. Such a response may indicate the presence of relatively viscous blood, because the rotor system generally assumes the new position with very little, if any, oscillation. For example, in another aspect of the present invention, dynamic behavior and stiffness quantification may be accomplished by applying a shock impulse to the pump while the rotor position is observed. The oscillations of the rotor may be measured and information about the damped natural frequency, the damping ratio, stiffness, and other information may be directly measured or calculated. In one embodiment, rotor position as a function of time may be measured and memorialized (e.g., via computer memory) and a differential equation for describing the motion of the rotor may be solved with respect to viscosity of the fluid interacting with the rotor. Such a differential equation may be iteratively or otherwise solved as known in the art, without limitation. Such a method may provide a relatively robust method for determining a viscosity of a fluid interacting with a rotor of a pump device.

It should be understood that the present invention further contemplates that a pump apparatus may include a system including a processor (e.g., an integrated circuit or so-called computer processor) that is configured for performing one or more of the following: the above-described energy measurements, rotor system parameter determinations, or other related calculations or analysis for carrying out the present invention. Such a system may form a portion of the control system for a pump device according to the present invention, if such a configuration is desired. Put another way, a pump device may include a rotor capable of magnetic suspension by way of an axial magnetic bearing, wherein the pump is configured for impelling fluid flow. Generally, a processor may be operably coupled to a controller and configured for estimating a viscosity of fluid within the pump by way of measuring an amount of energy relative to a response of a rotor to a change in an axial setpoint during a selected time period. In one example, such a system may include a controller for selectively providing a magnitude of electric current to the axial magnetic bearing according to a control algorithm implemented therewith, wherein a processor is operably connected to the controller and configured for estimating a viscosity of fluid within the pump by way of measuring an amount of energy provided to the axial magnetic bearing during a selected time period. Of course, the actions of estimating a viscosity of fluid within the pump or measuring an amount of energy provided to the axial magnetic bearing during a selected time period may be in accordance with any of the methods described hereinabove.

While certain embodiments and details have been included herein and in the attached invention disclosure for purposes of illustrating the invention, it will be apparent to those skilled in the art that various changes in the methods and apparatus disclosed herein may be made without departing form the scope of the invention, which is defined in the appended claims. Further, as mentioned above, while many of the above-described embodiments have been discussed herein with respect to blood pumps, the present invention contemplates that any pump utilizing a suspended rotor may practice the methods or employ apparatuses according to present invention. Additionally, the words "including" and "having," as used herein, including the claims, shall have the same meaning as the word "comprising."

What is claimed is:

1. A method for determining a viscosity of a fluid interacting with a rotor of a pump, the method comprising:
providing a fluid pump including a rotor exhibiting a first axial setpoint;
causing the rotor to respond to a second axial setpoint from the first axial setpoint by supplying energy to an axial magnetic bearing;
determining an amount of energy supplied to the axial magnetic bearing associated with causing the rotor to respond to the second axial setpoint from the first axial setpoint;
correlating the amount of energy with a viscosity of a fluid interacting with the rotor to determine the viscosity of the fluid interacting with the rotor.

2. The method of claim 1, wherein determining the amount of energy supplied to the axial magnetic bearing comprises calculating an amount of electrical energy supplied to the axial magnetic bearing.

3. The method of claim 2, wherein calculating the amount of electrical energy supplied to the axial magnetic bearing comprises mathematically integrating, over a selected time period, a current supplied to the axial magnetic bearing.

4. The method of claim 1, wherein determining the amount of energy associated with causing the rotor to respond to the second axial setpoint comprises correcting for losses of the amount of energy supplied to the axial magnetic bearing.

5. The method of claim 1, further comprising indicating the presence of an obstruction in fluid communication with the pump by determining the viscosity of the fluid interacting with the rotor.

6. The method of claim 1, wherein causing the rotor to respond to the second axial setpoint further comprises rotating the rotor.

7. The method of claim 1, further comprising rotating the rotor.

8. The method of claim 1, wherein exhibiting the first axial setpoint comprises allowing the rotor to be unsuspended.

9. The method of claim 1, wherein causing the rotor to respond to the second axial setpoint from the first axial setpoint comprises supplying a current supplied to an axial magnetic bearing by way of an automatic control system.

10. The method of claim 1, wherein determining the amount of energy associated with causing the rotor to respond to the second axial setpoint from the first axial setpoint comprises determining an amount of energy associated with at least a portion of an axial oscillation of the rotor.

11. The method of claim 1, wherein causing the rotor to respond to the second axial setpoint comprises causing the rotor to overshoot the second axial setpoint.

12. The method of claim 1, wherein determining the amount of energy associated with causing the rotor to respond to the second axial setpoint from the first axial setpoint comprises determining an amount of energy supplied to an axial magnetic bearing during a selected time period.

13. The method of claim 1, wherein determining the amount of energy associated with causing the rotor to respond to the second axial setpoint from the first axial setpoint comprises determining an amount of energy supplied to an axial magnetic bearing during a selected time period subsequent to the rotor exhibiting the first axial setpoint.

14. The method of claim 13, wherein determining the amount of energy associated with causing the rotor to respond to the second axial setpoint comprises determining an amount of energy supplied to an axial magnetic bearing during a time period defined between any two of the following: an initial time, a time associated with a cross over point, a time associated with a maximum overshoot, and a time associated with an axial position of the rotor being within 5% of the second axial setpoint.

15. The method of claim 1, further comprising:
operating the fluid pump;
calculating a flow rate of fluid passing through the fluid pump based on the determined viscosity of the fluid.

16. The method of claim 1, further comprising:
causing the rotor to exhibit a third axial setpoint;
determining another amount of energy associated with causing the rotor to respond to the third axial setpoint;
correlating the another amount of energy with another viscosity of the fluid to determine the viscosity of the fluid interacting with the rotor.

17. A method for determining a viscosity of a fluid interacting with a rotor, wherein the rotor is configured for impelling the fluid, the method comprising:
providing a fluid pump having a rotor that is initially unsuspended by supplying energy to an axial magnetic bearing;
suspending the rotor subsequent to the rotor being unsuspended;
determining an amount of energy supplied to the axial magnetic bearing associated with suspending the rotor subsequent to the rotor being unsuspended;
correlating the amount of energy with a viscosity of a fluid interacting with the rotor to determine the viscosity of the fluid interacting with the rotor.

18. The method of claim 17, wherein providing the fluid pump having the rotor that is initially unsuspended comprises providing the fluid pump having the rotor that is initially unsuspended and at rest.

19. The method of claim 17, wherein determining the amount of energy supplied to an axial magnetic bearing comprises calculating an amount of electrical energy supplied to the axial magnetic bearing.

20. The method of claim 19, wherein calculating the amount of electrical energy supplied to the axial magnetic bearing comprises mathematically integrating, over a selected time period, a current supplied to the axial magnetic bearing.

21. The method of claim 17, wherein determining the amount of energy for suspending the rotor comprises correcting for losses of the amount of energy supplied to the axial magnetic bearing.

22. The method of claim 17, further comprising indicating the presence of an obstruction in fluid communication with the pump by determining the viscosity of the fluid interacting with the roter.

23. The method of claim 17, further comprising rotating the rotor.

24. The method of claim 17, wherein suspending the rotor subsequent to the rotor being unsuspended comprises supplying a current to an axial magnetic bearing by way of an automatic controller.

25. The method of claim 17, wherein determining the amount of energy associated with suspending the rotor comprises determining an amount of energy associated with at least a portion of an axial oscillation of the rotor.

26. The method of claim 17, wherein suspending the rotor comprises causing the rotor to overshoot the second axial setpoint.

27. The method of claim 17, wherein determining the amount of energy associated with suspending the rotor comprises determining an amount of energy supplied to the axial magnetic bearing for a selected time period.

28. The method of claim 17, wherein determining the amount of energy associated with suspending the rotor comprises determining an amount of energy supplied to the axial magnetic bearing for a selected time period subsequent to the rotor being unsuspended.

29. The method of claim 28, wherein determining the amount of energy associated with suspending the rotor comprises determining an amount of energy associated with a time period between any two of the following:

an initial time, a time associated with a cross over point, a time associated with a maximum overshoot, and a time associated with an axial position of the rotor being within 5% of the second axial setpoint.

30. The method of claim 17, further comprising:
operating the fluid pump:
calculating a flow rate of fluid passing through the fluid pump based on the determined viscosity of the fluid.

31. The method of claim 17, further comprising:
allowing the rotor to become unsuspended after suspending the rotor by changing energy supplied to an axial magnetic bearing;
repeating suspending the rotor;
determining an amount of energy supplied to the axial magnetic bearing associated with repeating suspending the rotor;
correlating the amount of energy with another viscosity of a fluid interacting with the rotor to determine the another viscosity of the fluid interacting with the rotor.

32. A method for determining a viscosity of a fluid interacting with a rotor, wherein the rotor is configured for impelling the fluid, the method comprising:
providing a fluid pump having a rotor;
axially moving the rotor by supplying energy to an axial magnetic bearing;
determining an amount of energy supplied to the axial magnetic bearing associated with axially moving the rotor during a selected time period;
correlating the amount of energy with a viscosity of a fluid interacting with the rotor to determine the viscosity of the fluid interacting with the rotor.

33. A method for determining a viscosity of a fluid interacting with a rotor, wherein the rotor is configured for impelling the fluid, the method comprising:
providing a fluid pump having a rotor;
non-impellingly moving the rotor by supplying energy to an axial magnetic bearing;
determining an amount of energy supplied to the axial magnetic bearing associated with non-impellingly moving the rotor during a selected time period;
correlating the amount of energy with a viscosity of a fluid interacting with the rotor to determine the viscosity of the fluid interacting with the rotor.

34. A method for determining a viscosity of a fluid interacting with a rotor, the method comprising:
suspending a rotor of a fluid pump by supplying energy to an axial magnetic bearing;
subsequent to suspending the rotor, allowing the rotor to become unsuspended by changing the energy supplied to the axial magnetic bearing;
quantifying an energy response of the rotor to a selected axial setpoint subsequent to allowing the rotor to become unsuspended so as to determine a viscosity of fluid passing through the pump.

35. The method of claim 1, wherein causing the rotor to respond to the second axial setpoint further comprises axial movement to the second axial setpoint from the first axial setpoint without rotating the rotor.

36. The method of claim 17, wherein suspending the rotor subsequent to the rotor being unsuspended comprises translational movement of the rotor without rotational movement of the rotor.

* * * * *

UNITED STATES PATENT AND TRADEMARK OFFICE
CERTIFICATE OF CORRECTION

PATENT NO.         : 7,578,782 B2                                    Page 1 of 1
APPLICATION NO. : 11/138041
DATED                 : August 25, 2009
INVENTOR(S)       : Scott D. Miles et al.

It is certified that error appears in the above-identified patent and that said Letters Patent is hereby corrected as shown below:

Title Page; item (75);
On the bibliography page of the patent, inventor "Gill B. Beamson" should read --Gill B. Bearnson--.

Column 6, line 48, "active"" should read --"active"--.

Column 8, line 53, "axial magnetic" should read --axial, magnetic--.

Column 8, line 56, "P0" should read --$P_0$--.

Column 8, line 57, "P1" should read --$P_1$--.

Column 8, line 60, "t0" should read --$t_0$--.

Column 8, line 61, "P0 to P1" should read --$P_0$ to $P_1$--.

Column 8, line 67, "x0" should read --$x_0$--.

Column 9, line 2, "P1" should read --$P_1$--.

Column 9, line 3, "P1" should read --$P_1$--.

Signed and Sealed this

Seventeenth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,578,782 B2
APPLICATION NO. : 11/138041
DATED : August 25, 2009
INVENTOR(S) : Miles et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 735 days.

Signed and Sealed this

Seventh Day of September, 2010

David J. Kappos
*Director of the United States Patent and Trademark Office*